United States Patent [19]

Largeau et al.

[11] Patent Number: 5,670,649
[45] Date of Patent: Sep. 23, 1997

[54] DERIVATIVES OF 2-AZABICYCLO[2.2.1] HEPTANE, THEIR PREPARATION AND THEIR APPLICATION

[75] Inventors: Denis Largeau, Taluyers; Patrick Leon, Tassin la Demi Lune, both of France

[73] Assignee: Rhone-Poulenc Rorer S.A., Antony, France

[21] Appl. No.: 655,395

[22] Filed: May 30, 1996

Related U.S. Application Data

[63] Continuation-in-part of Ser. No. 476,156, Jun. 7, 1995.

[30] Foreign Application Priority Data

May 30, 1995 [FR] France .................................. 95 06353

[51] Int. Cl.⁶ .......................... C07D 31/40; C07D 31/41
[52] U.S. Cl. ......................... 548/431; 548/452; 548/512
[58] Field of Search ............................. 548/452, 431, 548/512

[56] References Cited

U.S. PATENT DOCUMENTS 5,364,862  11/1994  Spada et al. ............................. 514/303

*Primary Examiner*—Joseph McKane
*Attorney, Agent, or Firm*—Raymond S. Parker, III; Martin F. Savitzky

[57] ABSTRACT

Novel derivatives of 1R- or 1S-2-azabicyclo[2.2.1]heptane with the general formula (I) or (I'), their preparation and their application.

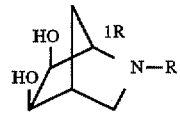

(I)

or

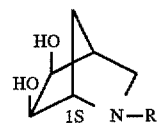

(I')

In the general formulas (I) and (I'), R represents a hydrogen atom or a group with the formula

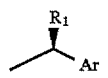

(II)

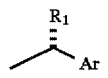

(II')

respectively, in which $R_1$ represents an alkyl group containing 1–4 carbon atoms and Ar represents an optionally substituted phenyl or α- or β-naphthyl group.

The novel products with the general formula (I) are particularly useful for the preparation of adenosine agonists.

9 Claims, No Drawings

DERIVATIVES OF 2-AZABICYCLO[2.2.1] HEPTANE, THEIR PREPARATION AND THEIR APPLICATION

This application is a continuation-in-part of U.S. patent application Ser. No. 08/476,156, filed Jun. 7, 1995, now abandoned.

The present invention relates to novel derivatives of 1R- or 1S-2-azabicyclo[2.2.1]heptane with the general formula

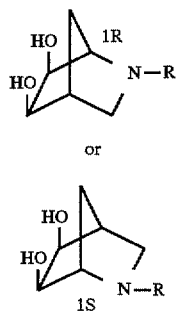

their preparation and their application.

In the general formulas (I) and (I'), R represents a hydrogen atom group or, respectively, a group with the general formula:

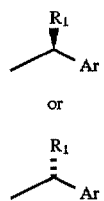

in which $R_1$ represents an alkyl group containing 1–4 carbon atoms and Ar represents a phenyl or α- or β-naphthyl group, optionally substituted by one or more identical or different atoms or groups selected from the halogen atoms and the alkyl groups containing 1–4 carbon atoms, alkoxy groups containing 1–4 carbon atoms, or nitro groups.

Preferably, $R_1$ represents a methyl or ethyl group, and Ar represents a phenyl group, which is optionally substituted by one or more methyl or methoxy groups.

Still more specifically, $R_1$ represents a methyl group, and Ar represents a phenyl group.

According to the invention, the products with the general formula (I) or (I') in which R represents, respectively, a group with the general formula (II) or (II') can be obtained by bis-hydroxylation of a product with the general formula:

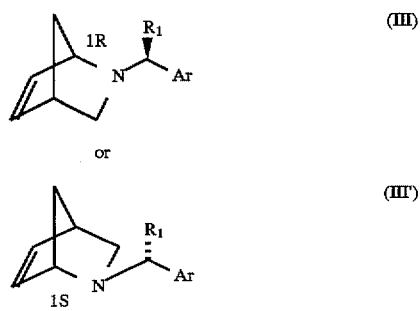

in which $R_1$ and Ar are defined as above.

In general, bis-hydroxylation is carried out by working under the conditions described by V. VanRheenen et al., Tetrahedron Letters, Vol. 23, 1973–1976 (1976). More particularly, the oxidation can be carried out by means of potassium permanganate or osmium tetroxide and working in the presence of N-methylmorpholine oxide or triethylamine oxide or potassium ferricyanide ($K_3FeCN_6$). A preferred embodiment according to the invention is using a catalytic amount of osmium tetraoxide. The reaction with the osmium may occur with as little as about 0.06% to about 1% which takes respectively from about 21 to about 5 hours. The oxidation may take place in an aqueous-organic medium such as water-t-butanol or water-acetone, more preferably water-acetone.

In general, the oxidant must be selected in such a manner that the 5,6-dihydroxy derivative is only formed in the exo form.

The product with the general formula (III) or (III') can be obtained by a Diels-Alder reaction between a homochiral amine with the general formula:

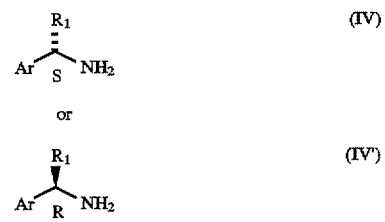

in which $R_1$ and Ar are defined as above, in the form of a salt, preferably with a mineral acid such as hydrochloric acid, formaldehyde and cyclopentadiene working under the conditions described by S. D. Larsen and P. A. Grieco, J. Amer. Chem. Soc., Vol. 107, 1768–1769 (1985).

The implementation of the method leads, starting from a homochiral amine with the R- or S- form, to a mixture of 2 diastereoisomers which react in the same manner in the subsequent bis-hydroxylation step, and therefore do not necessarily have to be separated.

According to the invention, the product with the general formula (I) or (I') in which R represents a hydrogen atom can be obtained by hydrogenolysis of a product with the general formula (I) or (I'), in which R represents a group with the general formula (II) or (II') by means of hydrogen in the presence of a catalyst such as palladium on charcoal working in an organic solvent such as an alcohol, for example, methanol.

Isomer 1R of general formula (I), in which R represents a radical of general formula (II), can be isolated from a mixture of products of general formulas (I) and (I') by diastereoselective crystallization with an optically-active organic acid such as L-dibenzoyl tartaric acid as described by C. K.-F. Chiu in Syn. Comm., 26(3), 577 (1996) or L-dimethoxysuccinic acid in an appropriate organic solven such as a ketone or an aliphatic alcohol. It is particularly advantageous to use L-dimethoxysuccinic acid in an isopropanol.

The novel products with the general formula (I) are particularly useful for the preparation of the products which are the object of U.S. Pat. No. 5,364,862 and which are active agents in the treatment of cardiovascular diseases, such as hypertension and myocardial ischemia.

[1-S[1a,2b,3b,4a(S*)]]-4-[7-[[2-(3-chloro-2-thienyl]-1-ethylethyl]amino]-3H-imidazo[4,5-b]pyridin-3-yl]-N-ethyl-2,3-dihydroxycyclopentanecarboxamide of the following formula is of particular interest:

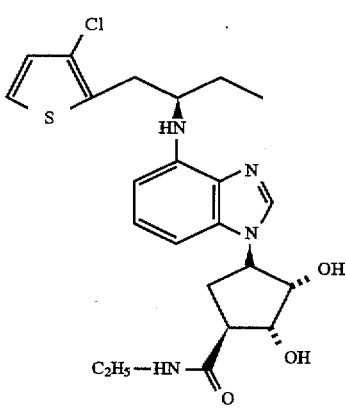

The products with the general formula (I) are particularly useful for the preparation of the carbo sugar with the general formula:

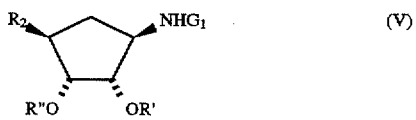

in which $R_2$ represents carboxy, alkoxycarbonyl whose alkyl moiety contains 1–4 carbon atoms, N-alkylaminocarbonyl whose alkyl moiety contains 1–4 carbon atoms, or hydroxymethyl or alkoxymethyl, and R' and R", which may be identical or different, represent a hydrogen atom or an aliphatic organic acid residue containing 2–4 carbon atoms, such as an acetyl or propionyl or aromatic acid group such as a benzoyl residue, or R' and R" together form a methylene group whose carbon atom is optionally substituted by one or more groups, which may be identical or different, selected from the alkyl groups containing 1–4 carbon atoms, which can combine to form alicyclic group containing 5 or 6 carbon atoms, or phenyl groups, and $G_1$ represents a hydrogen atom or a protecting group $G_2$ for the amino function. More particularly, R2 represents an ethylaminocarbonyl group or hydroxymethyl group, and R' and R" together form an isopropylidene group.

The carbo sugar with the general formula (V) constitutes one of the structural elements of the products claimed in U.S. Pat. No. 5,364,862.

The preparation of the carbo sugar with the general formula (V) from the product with the general formula (I) can be achieved as follows.

The hydroxy functions of the product with the general formula (I), in which R represents a hydrogen atom or a group with the general formula (II), can be protected in the form of an ester or acetal to yield a product with the general formula:

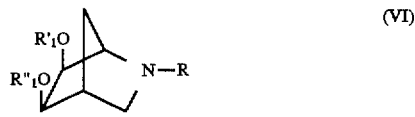

in which R represents a hydrogen atom or a group with the general formula (II) and $R'_1$ and $R''_1$, which may be identical or different, represent an aliphatic organic acid residue containing 2–4 carbon atoms, such as an acetyl or propionyl group or an aromatic acid such as a benzoyl residue, or $R'_1$ and $R''_1$ together form a methylene group whose carbon atom is optionally substituted by one or more groups, which may be identical or different, selected from the alkyl groups containing 1–4 carbon atoms, which together can form an aliphatic group containing 5 or 6 carbon atoms, or phenyl groups.

In general, the protection of the hydroxy groups is achieved under the usual esterification or acetalization conditions, for example, by reacting acetic acid or propionic acid in the presence of p-toluenesulfonic acid in an organic solvent such as an aromatic hydrocarbon, for example, benzene or toluene, by separating the water gradually as it is formed or by reacting an aldehyde or a ketone, possibly in the form of an acetal, in the presence of an acid such as trifluoroacetic acid in an organic solvent such as an aliphatic alcohol, for example, 2-propanol (IPA), aromatic hydrocarbon, for example, benzene or toluene, at about 50° C. to the boiling point of the reaction mixture. A preferred acetalization medium comprises 2,2-dimethoxypropane, trifluoroacetic acid and IPA at a temp[erature of about 70° C.

The product with the general formula (VI) in which R represents a group with the general formula (II) can be transformed into a product with the general formula (VI) in which R represents a hydrogen atom by hydrogenolysis.

In general, the hydrogenolysis is carried out by means of hydrogen, which is optionally pressurized, in the presence of a catalyst such as palladium on charcoal in an organic solvent such as an alcohol, for example, methanol, ethanol or isopropanol, at a temperature between 0° and 50° C.

The product with the general formula (VI), which is a model product, constitutes another subject of the present invention.

The product with the general formula (VI) in which R represents a hydrogen atom can be transformed into a product with the general formula:

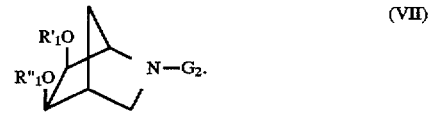

in which $R'_1$ and $R''_1$ are defined as before and $G_2$ represents a protecting group for the amino function by a reaction with an appropriate reagent which allows the selective introduction of a protecting group.

The protecting groups are selected from those which can later be eliminated selectively. These protecting groups include the following, which are particularly well suited: the chloroacetyl, methoxymethyl, trichloro-2,2,2-ethoxycarbonyl, t-butyl, benzyl, p-nitrobenzyl, p-methoxybenzyl, diphenylmethyl, trialkylsilyl, allyloxycarbonyl, benzyloxycarbonyl groups, in which the phenyl ring is optionally substituted by a halogen atom or by an alkyl group containing 1–4 carbon atoms or alkoxy group containing 1–4 carbon atoms, or t-butoxycarbonyl. Among the protecting groups which are particularly well suited, one can mention those described by T. W. Greene and P. G. M. Wuis, "Protecting Groups in Organic Synthesis," Chapter 7, 2nd edition, John Wiley & Sons (1991).

The t-butoxycarbonyl group is of particular interest.

The product with the general formula (VII) in which $G_2$ represents a t-butoxycarbonyl group can be obtained directly from a product with the general formula (VI) in which R represents the group with the general formula (II) by simultaneous hydrogenolysis and t-butoxycarbonylation.

In general, the reaction is carried out by simultaneously reacting the hydrogen in the presence of a catalyst such as palladium and charcoal and di-t-butyl dicarbonate with a product with the general formula (VI) working in an organic solvent such as an alcohol, for example, methanol, ethanol or isopropanol, at a temperature between 0° and 50° C.

The product with the general formula (VII) is a novel product which constitutes another embodiment of the present invention.

The product with the general formula (VII) is then oxidized into a product with the general formula:

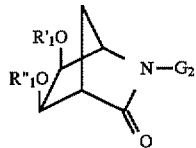

(VIII)

in which R'₁, R"₁ and G₂ are defined as above.

In general, the oxidation is conducted by means of a ruthenium oxide (RuO₄), which can be optionally generated in situ from a precursor such as RuO₂ or RuCl₃ in the presence of an oxidant selected from a periodate such as sodium periodate, a hypochlorate such as hypochlorite or sodium hypobromite or a bromate such as sodium bromate or an organic tertiary amine oxide such as N-methylmorpholine oxide or triethylamine oxide, working in water or in homogeneous or heterogeneous aqueous-organic medium, such as a water-ethyl acetate mixture.

The oxidation can also be conducted using sodium hypochlorite alone (javelle) or using potassium permanganate or sodium tungstate in the presence of an oxidant such as sodium hypochlorite, hydrogen peroxide or an alkyl hydroperoxide.

The product with the general formula (VIII) can also be obtained by oxidation of a product with the general formula (VI) in which R represents a hydrogen atom under the conditions described above, followed by the protection of the nitrogen atom of the lactam obtained with the general formula:

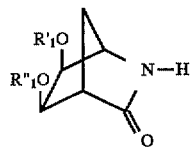

(IX)

in which R'₁ and R"₁ are defined as above, by a protecting group as defined above.

The product with the general formula (VIII) is a novel product which constitutes another subject of the present invention.

The product with the general formula (VIII) can be transformed into a product with the general formula (V) under conditions which are appropriate for the nature of the substituent R₂ which must be introduced.

The product with the general formula (V) in which R2 represents a carboxy group can be prepared by reacting a mineral base such as sodium hydroxide with the product with the general formula (VIII), followed by the replacement of the protecting group G₂ by a hydrogen atom and optionally groups R'₁ and R"₁ by hydrogen atoms.

The product of general formula (V), in which R₂ represents a carboxy group, can be obtained by the replacement of the protective group G₂ of general formula (VIII) with a hydrogen atom, followed by the action of a mineral base such as sodium carbonate, and optionally replacing the radicals R'₁ and R"₁ by hydrogen atoms.

The product with the general formula (V) in which R₂ represents an alkoxycarbonyl group whose alkyl moiety contains 1–4 carbon atoms can be prepared by reacting an alcoholate of an alkali metal with the product with the general formula (VIII), followed by the replacement of the protecting group G₂ by a hydrogen atom and optionally of the groups R'₁ and R"₁ by hydrogen atoms.

The product of general formula (V), in which R₂ represents an alkoxycarbonyl radical, the alkoyl portion of which contains 1 to 4 carbon atoms, can be obtained by the replacement of the protective group G₂ of the product of general formula (VIII) by a hydrogen atom, followed by the action of an alcoholate of an alkaline metal, and optionally replacing the radicals R'₁ and R"₁ by hydrogen atoms.

The product with the general formula (V) in which R₂ represents an N-alkylaminocarbonyl group whose alkyl moiety contains 1–4 carbon atoms can be prepared by reacting an alkylamine with the product with the general formula (VIII), followed by the replacement of the protecting group G₂ by a hydrogen atom and optionally of the groups R'₁ and R"₁ by hydrogen atoms.

The product of general formula (V), in which R₂ represents an N-alkoylaminocarbonyl radical, the alkoyl portion of which contains 1 to 4 carbon atoms, can be obtained by the replacement of the protective group G₂ of the product of general formula (VIII) by a hydrogen atom, followed by the action of an alkoylamine, and optionally replacing the radicals R'₁ and R"₁ by hydrogen atoms.

The product with the general formula (V) in which R₂ represents a hydroxymethyl group can be prepared by reacting a reducing agent such as a borohydride, for example, sodium or potassium borohydride, with the product with the general formula (VIII), followed by the replacement of the protecting group G₂ by a hydrogen atom and optionally of the groups R'₁ and R"₁ by hydrogen atoms.

The product of general formula (V), in which R₂ represents a hydroxymethyl radical, can be obtained by replacement of protective group G₂ of the product of general formula (VIII) by a hydrogen atom, followed by the action of a reducing agent such as sodium or potassium borohydride, and optionally replacing the radicals R'₁ and R"₁ by hydrogen atoms.

The product with the general formula (V) can be used under the conditions described in U.S. Pat. No. 5,364,862 to produce the therapeutically active products.

The present invention is further Exemplified but not limited by the following illustrative Examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1a

Preparation of 2-(α-S-Methylbenzyl)-2-azabicyclo [2.2.1]hept-5-ene

In a 2L reactor is charged 255 g of (S)-(−)-α-methylbenzylamine and 300 mL of water. The suspension is cooled to −5° C. and a solution of 185 mL of concentrated HCl in 100 mL of water is added with stirring over one hour. The pH of the mixture is adjusted to between 5 and 6.5. Stirring is continued for 30 minutes and then 242 mL of 37% formaldehyde solution is charged. After stirring for an additional 40 minutes, cyclopentadiene (~270 mL) is distilled directly into the reaction mixture. The resultant mixture is stirred vigorously overnight at −5° C. The completion of the reaction is determined by HPLC. Two layers separated and the aqueous layer is washed with 250 mL of heptane before basifying to a pH of 11 with 168 mL of 50% NaOH solution and crushed ice. The organic mixture is then extracted with 2×500 mL and 2×300 mL portions of EtOAc. The combined extracts are washed with 200 mL of cold water, followed by 200 mL of saturated NaCl solution, dried over anhydrous $Na_2SO_4$ and filtered. The clear filtrate is concentrated by rotory evaporation to yield 408.4 g (97.4%) of a yellow oil, 2-(α-S-Methylbenzyl)-2-azabicyclo-[2.2.1] hept-5-ene e, in a diastereomeric ratio=77.1%:22.9% in favor of the desired isomer.

$^1$H NMR (500 MHz, CDCl$_3$): δ1.35 (d, 2H); 1.46 (d, 1H); 1.62 (d, 1H); 2.89 (d, 1H); 3.05 (m, 1H); 4.13 (s, 1H); 6.32 (m, 1H); 7.26 (d, 2H); 7.33 (d, 2H); MS (EI, 70 eV) m/z (relative intensity): 199 (M+, 70)

EXAMPLE 1b

Preparation of 2-(α-S-Methylbenzyl)-2-azabicyclo [2.2.1]hept-5-ene

Into a 250-mL three-necked flask equipped with a cooling apparatus and stirring system, a solution is introduced under an argon atmosphere, which solution consists of 20 g of α-S-methylbenzylamine (165 mmol) in 60 mL of water whose pH is adjusted to 6.10 by the addition of 17 mL of 36% hydrochloric acid (W/V). After cooling to 5° C., 20 mL of a 37% (W/V) aqueous formaldehyde solution are added. The solution is stirred for 5 minutes at 5° C.; then 21.8 g of cyclopentadiene (330 mmol) are added. The mixture is stirred for 16 hours between −5° and 0° C. The aqueous phase is separated by decanting and then washed with 50 mL of pentane. The neutralization to pH=8.0 is achieved by addition of concentrated sodium hydroxide. Two extractions are then carried out, each with 70 mL of ethyl acetate. The pH of the aqueous phase is adjusted to 11 by the addition of concentrated sodium hydroxide, followed by two extractions, each with 70 mL of ethyl acetate. The organic phases are combined, and then washed two times with 50 mL of water, and then they are dried over sodium sulfate. After filtration and concentration to dryness at a reduced pressure, the yield consists of 33.10 g of 2-(α-S-methylbenzyl)-2-azabicyclo[2.2.1]hept-5-ene in the form of a slightly yellow oil.

EXAMPLE 2a

Preparation of 5R,6S-Dihydroxy-2-(α-S-methylbenzyl)-2-azabicyclo-[2.2.1]heptane

Into a 500-mL three-necked flask equipped with a cooling apparatus and a stirring system, containing a solution of 20 g of 2-(α-S-methylbenzyl)-2-azabicyclo[2.2.1]hept-5-ene (75.34 mmol) in 220 mL of t-butanol, 12 g of N-methylmorpholine oxide in 32 mL of water, at a temperature of approximately 25° C., are added, then 6.3 mL of a 25% (W/V) solution of osmium tetroxide (OsO$_4$) in t-butanol are added slowly. The stirring is continued for 2 hours at a temperature of approximately 20° C., then for 3 hours at 65° C. After evaporation of the t-butanol at a reduced pressure, the residue is redissolved in 350 mL of isopropanol. After concentration to dryness at a reduced pressure, 24 g of cis-5,6-dihydroxy-2-(α-S-methylbenzyl)-2-azabicyclo[2.2.1]heptane are produced in the form of an oil. 14 g of 5R,6S-dihydroxy-2-(α-S-methylbenzyl)-2-azabicyclo[2.2.1]heptane are produced by crystallization in cyclohexane, with an isomeric purity of more than 95%.

The NMR spectrum, determined in deuterochloroform, shows the following shifts (δ): 1.21 (3H, d); 1.38 (1H, d); 1.59 (1H, d); 2.22 (2H, m); 2.45 (1H, dd); 2.95 (1H, s); 3.99 (1H, q); 3.78 (1H, d); 3.90 (1H, d); 7.28 (5H, m).

EXAMPLE 3b

Preparation of 5R,6S-Dihydroxy-2-(α-S-methylbenzyl)-2-azabicyclo-[2.2.1]heptane

A solution of 0.5 mmols of a mixture (78/22 in mols) of 5R,6S-dihydroxy-2-(α-S-methylbenzyl)-2-azabicyclo [2.2.1]heptane and 5S,6R-dihydroxy-2-(α-S-methylbenzyl) -2-azabicyclo[2.2.1]heptane and 0.5 mmols of L-dimethoxysuccinic acid in 1 mL of isopropanol is stirred for 24 hours at a temperature ranging from 25° C. at the beginning to 5° C. The crystals obtained are separated by filtration and dried. One thus obtains 110 mg of 5R,6S-dihydroxy-2-(α-S-methylbenzyl)-2-azabicyclo[2.2.1] heptane with an enantiomeric excess of 97%.

The mixture of 5R,6S-dihydroxy-2-(α-S-methylbenzyl)-2-azabicyclo-[2.2.1]heptane and 5S,6R-dihydroxy-2-(α-S-methylbenzyl)-2-azabicyclo[2.2.1]heptane (78/22 in mols) may be obtained in the following manner:

In a 250 mL three-necked round-bottom flask provided with a coolant and a stirring system, containing a solution of 7 g 2-(α-S-methylbenzyl)-2-azabicyclo[2.2.1]hept-5-ene (35 mmols) in 70 mL of t-butanol, is added, at a temperature of approximately 25° C., 4.12 g of N-methylmorpholine oxide in 11 mL of water, then, 360 ml of a 2.5% solution (p/v) of osmium tetroxide (OsO$_4$) in t-butanol is slowly added. The mixture is stirred for 1 hour at a temperature of approximately 20° C., and then for 4 hours at 65° C. After the evaporation of the t-butanol under reduced pressure, the residue is taken up in 150 mL of isopropanol. After concentrating until dry under reduced pressure, one obtains 8.27 g of a product, the N.M.R. spectrum of the proton of which shows that it is composed of a mixture (78/22 in mols) of 5R,6S-dihydroxy-2-(α-S-methylbenzyl)-2-azabicyclo [2.2.1]heptane and 5S,6R-dihydroxy-2-(α-S-methylbenzyl) -2-azabicyclo[2.2.1]heptane.

EXAMPLE 3c

Preparation of 5R,6S-Dihydroxy-2-(α-S-methylbenzyl)-2-azabicyclo-[2.2.1]heptane L-tartrate To a 2L reactor is charged 210 g of 2-(α-S-methylbenzyl) -2-azabicyclo[2.2.1]hept-5-ene, 1,200 mL of 2-methyl-2-propanol and 182 mL of 4-methymorpholine N-oxide. To this mixture is charged, in dropwise fashion, 8 mL of a 2.5% solution of osmium tetroxide in 2-methy-2-propanol. Under nitrogen the mixture is heated to 62° C. with vigorous stirring for 22 hours. The reaction mixture is concentrated by rotary evaporation at 60° C. 300 mL of IPA is charged and the solution is again concentrated at 60° C. to yield 246 g of 5R,6S-Dihydroxy-2-(α-S-methylbenzyl)-2-azabicyclo-[2.2.1]heptane L-tartrate as a dark brown syrup. The crude product is suspended in 1.8L of 75% IPA at 40° C. To the suspension is added 158.2 g of L-tartaric acid with vigorous stirring. Agitation is continued at 40° C. for 2.5 hours. The mixture is cooled to 30° C., filtered, washed with 500 mL of 75% IPA and 200 mL of IPA, then dried at 70° C. in vacuo for 16 hours to give 269.5 g of the desired L-tartrate salt as a cream colored solid (MP 143°–145° C., diastereomeric ratio—94.2%:5.8% ).

$^1$H NMR (500 MHz, CDCl3): δ1.3 (d, 3H); 2.5 (m, 2H); 4.18 (s, 2H); 7.36 (t, 2H); 7.4 (t, 2H); MS (EI, 70 eV) m/z (relative intensity): 233 (M+, 13)

EXAMPLE 4a

Preparation of 5R,6S-isopropylidenedioxy-2-(α-S-methylbenzyl)-2-azabicyclo-[2.2.1]heptane Into 500-mL three-necked flask, equipped with a cooling apparatus and a stirring system, containing a solution of 18.4 g of 5R,6S-dihydroxy-2-(α-S-methylbenzyl)-2-azabicyclo [2.2.1]heptane (76 mmol) in 130 mL of toluene, 31.7 g of 2,2-dimethoxypropane (304 mmol) and then 13 g of trifluoroacetic acid are added slowly (114 mmol). The mixture is heated for 4 hours 10 minutes at 65° C. After cooling to 30° C. and concentration in the rotary evaporator to eliminate the toluene, the excess 2,2-dimethoxypropane and partially the trifluoroacetic acid, the reaction mixture is taken up in dichloromethane, then it is neutralized by the addition of 100 mL of 2N sodium hydroxide. After decanting, drying of the organic phase over sodium sulfate, filtration, treatment with decolorizing charcoal (30 g) for 30 minutes at the boiling point of dichloromethane, filtration through clarcel [possibly a trade name] and concentration to dryness at reduced pressure, the yield consists of 18.8 g of 5R,6S-isopropylidenedioxy-2-(α-S-methylbenzyl)-2-azabicyclo-[2.2.1]heptane, whose structure is confirmed by the proton NMR spectrum, which, determined in deuterochloroform, shows the following shifts (δ): 1.22 (3H, d); 1.23 (6H, s); 1.31 (1H, d); 1.57 (1H, d); 2.08 (1H, d); 2.34 (1H, broad s); 2.45 (1H, dd); 3.06 (1H, s); 3.40 (1H, q); 4.09 (1H, d); 4.19 (1H, d); 7.26 (5H, m).

EXAMPLE 4b

Preparation of 5R,6S-isopropylidenedioxy-2-(α-S-methylbenzyl)-2-azabicyclo-[2.2.1]heptane To a 2-liter, 4-neck, jacketed cylindrical reactor equipped with a thermocouple, overhead stirrer and condenser is charged 223 g of 5R,6S-dihydroxy-2-(α-S-methylbenzyl)-2-azabicyclo[2.2.1]heptane L-tartrate followed by 1200 mL 2-propanol (IPA). Agitation is begun and the flask charged 286 mL of 2,2-dimethoxypropane and 44.6 mL of trifloroacetic acid (TFA). The suspension is heated to 72° C. until all the solids dissolved. After 5 hours, the reaction is cooled to 65° C. and the contents transferred to a 3L round bottom flask. Approximately 1100 mL of solvent is removed at 48° C. and 124 mbar vacuum. To the original 2-liter, 4-neck, jacketed cylindrical reactor is added 1.2L of 2M NaOH with stirring at 25° C. To the NaOH solution, is charged the residue from the distillation described above (ca. 700 mL of solution). The tan solution is cooled to 25° C. over 40 minutes. Solids begin to precipitate from the solution at 28° C. The suspension is stirred several hours before being filtered through an 11 cm Buchner funnel fitted with Whatman #1 filter paper. The filter cake is washed with 300 mL of water. The off-white solids are slurried in water for 13 hours and refiltered, washed with water and air dried. The solids are then vacuum dried at 50° C. to yield 112 g of 5R,6S-isopropylidenedioxy-2-(α-S-methylbenzyl)-2-azabicyclo[2.2.1]heptane as a white solid which according to HPLC is diastereomerically pure.

$^1$H NMR (500 MHz, CDCl$_3$): δ1.28 (s, 3H); 1.27 (d, 3H); 1.39 (s, 3H); 1.63 (d, 1H); 2.27 (d, 1H); 2.4 (d, 1H); 2.51 (dd, 1H); 3.12 (s, 1H); 3.46 (q, 1H); 4.2 (dd, 2H); 7.28 (m, 5H); MS (EI, 70 eV) m/z (relative intensity): 273 (M+, 8.4)

EXAMPLE 5a

Preparation of 5R,6S-isopropylidenedioxy-2-(t-butoxycarbonyl)-2-azabicyclo-[2.2.1]heptane In a 250-mL three-necked flask equipped with a stirring system, 0.5 g of 5% palladium on charcoal, 5 g of 5R,6S-isopropylidenedioxy-2-(α-S-methylbenzyl)-2-azabicyclo [2.2.1]heptane, 3.98 g of di-t-butyl dicarbonate and 36 mL of methanol. The apparatus is purged with argon and then with hydrogen, and then it is placed under a hydrogen atmosphere at 25° C. The reaction is continued for 5 hours by carrying out a purge with hydrogen every 15 minutes to eliminate the carbon dioxide formed.

After filtration through clarcel and concentration to dryness at a reduced pressure, the yield consists of 4.84 g of 5R,6S-isopropylidenedioxy-2-(t-butoxycarbonyl)-2-azabicyclo[2.2.1]heptane, whose structure is confirmed by the NMR spectrum, which, determined in dimethyl sulfoxide-d6, shows the following chemical shifts (δ): 1.16 (s, 3H); 1.28 (s, 3H); 1.32 (s, 1H); 1.34 (s, 3H); 1.65 (d, 1H); 2.38 (m, 1H); 2.65 (d, 1H); 2.99 (m, 1H); 3.84 (m, 1H); 3.94 (d, 1H); 4.16 (d, 1H).

EXAMPLE 5b

Preparation of 5R,6S-isopropylidenedioxy-2-(t-butoxycarbonyl)-2-azabicyclo-[2.2.1]heptane To a 2-liter, 4-neck, jacketed, cylindrical reactor equipped with a thermocouple, overhead stirrer, gas bladder and a septum for nitrogen and hydrogen inlet is charged in succession; 140 g of 5R,6S-isopropylidenedioxy-2-(α-S-methylbenzyl)-2-azabicyclo[2.2.1]heptane, 13.4 g of 10% Pd/C and 900 mL of methanol. The stirred suspension is stirred with nitrogen for 10 minutes followed by hydrogen for 10 minutes at 25° C. This procedure is repeated every 30 minutes and the reaction is monitored by TLC (Silica gel, Ethyl acetate, visualized with iodine). After 3 hours, the reaction is 50% complete according to TLC. To this partially reduced solution is charged 56 g of di-tert-butyldicarboxylate over 10 minutes followed by a nitrogen/hydrogen sparge as described above. Every 30 minutes, an additional 10 g of di-tert-butyldicarboxylate is added, followed by a nitrogen/hydrogen sparge until a total of 112 g of di-tert-butyldicarboxylate is added (56 g plus 10 g charges). The reaction mixture is stirred overnight at 25° C. The Pd/C suspension is filtered through a 9 cm Buchner funnel fitted with #54 filter paper and a bed of 5 g of celite and the reactor and filter cake are washed with 100 mL of methanol. The filtrate is placed in 2 liter 1-neck round bottom flask and 750 mL of solvent is removed at 40° C. and 105 mbar (ca. 250 mL of a light yellow solution remained). To the original reaction vessel, is charged 1L of water which is cooled to 10° C. The yellow residue from the above distillation is added to the cold water in virtually one portion. 5R,6S-Isopropylidenedioxy-2-(t-butoxycarbonyl)-2-azabicyclo[2.2.1]heptane precipitates from the solution as a white solid. The slurry is stirred for 30 minutes at 6° C. before filtering and washing with water. The resulting white solids are vacuum dried at 60° C. to yield 129.6 g of white solid which according to chiral HPLC is enantiomerically pure.

$^1$H NMR (500 Mhz, CDCl$_3$): δ1.28 (s, 3H); 1.4 (s, 3H); 1.45 (s, 9H); 1.87 (d, 1H); 2.53 (s, 1H); 2.82 (d, 1H); 3.17 (dd, 1H); 4.09 (m, 2H); 4.2 (m, 2H); MS (FAB-LRP) m/z (relative intensity): 270 ((M+H)+, 9.4)

EXAMPLE 6a

Preparation of 5R,6S-isopropylidenedioxy-2-(t-butoxycarbonyl)-2-azabicyclo-[2.2.1]heptan-3-one In a 30-mL tube, 270 mg of 5R,6S-isopropylidenedioxy-2-(t-butoxycarbonyl)-2-azabicyclo[2.2.1]heptane (1 mmol)

and 40 mg of $RuO_2 \cdot H_2O$ (0.3 Eq) are introduced. 10 mL of ethyl acetate and 720 mg of water (40 Eq) are added. Then, 2.14 g of sodium periodate (10 Eq) are added, and the tube is sealed hermetically. The stirring is continued for 16 hours at 50° C. The reaction mixture is filtered through clarcel, and then two extractions are carried out, each with 20 mL of ethyl acetate. The organic phases are dried over sodium sulfate. After the filtration and concentration to dryness at a reduced pressure, 245 mg of a solid are obtained, containing 68% of 5R,6S-isopropylidenedioxy-2-(t-butoxycarbonyl)-2-azabicyclo[2.2.1]heptan-3-one and 32% of starting material. The structure of the product obtained is confirmed by the NMR spectrum, which, determined in dimethyl sulfoxide $d_6$, shows the following chemical shifts (δ): 1.38 (9H, s); 1.23 (3H, s); 1.33 (3H, s); 1.85 (1H, d); 1.93 (1H, d); 2.69 (1H, s); 4.24 (1H, s); 4.41 (1H, d); 4.51 (1H, d).

EXAMPLE 6b

Preparation of 5R,6S-isopropylidenedioxy-2-(t-butoxycarbonyl)-2-azabicyclo-[2.2.1]heptan-3-one To a 2 liter 4-neck jacketed cylindrical reactor equipped with a thermocouple, overhead stirrer, and condenser is charged in succession: 120 g of 5R,6S-isopropylidenedioxy-2-(t-butoxycarbonyl)-2-azabicyclo[2.2.1]heptane, 0.3 g of ruthenium IV oxide, 201.2 g of sodium bromate, 960 mL of ethyl acetate, and 1000 mL of water with stirring. The reaction mixture is heated to 45° C. and stirred at this temperature for 15 hours. The stirring is discontinued and the aqueous layer discarded. Saturated NaCl (500 mL) is added to the reaction vessel and the suspension is stirred for 10 minutes. Stirring is again discontinued, the layers are allowed to separate and the aqueous layer removed. A 33% maleic acid disodium salt solution (500 mL) is charged to the reaction vessel, the suspension stirred for 5 minutes and the layers again separated. The organic layer is then filtered through a bed of Celite to remove the catalyst and the solvent is removed in vacuo. The resulting solid is dried in a vacuum oven to yield 117 g of 5R,6S-isopropylidenedioxy-2-(t-butoxycarbonyl)-2-azabicyclo[2.2.1]heptan-3-one as a white solid contaminated with 5% starting material. A 115 g sample of this material is dissolved in 350 mL of heptane at 85° C. and allowed to cool to 25° C. over about 3 hours then to 5° C. before filtration and drying in vacuo at 60° C. 92 g (74%) of 5R,6S-isopropylidenedioxy-2-(t-butoxycarbonyl)-2-azabicyclo-[2.2.1]heptan-3-one is obtained as a white crystalline solid.

$^1$H NMR: δ1.32 (m, 3H); 1.48 (m, 12H); 1.82 (m, 1H); 2.1 (m, 1H); 4.43 (m, 1H); 4.48 (m, 1H); 4.6 (m, 1H); MS (FAB-LRP in nitrobenzyl alcohol): 284 ((M+H)+, 10%)

EXAMPLE 7a

Preparation of 2R,3S-isopropylidenedioxy-4R-amino-1S-ethylaminocarbonyl cyclopentane benzoate In a 'Berghoff' tube is placed 568 mg of 5R,6S-isopropylidenedioxy-2-(t-butoxycarbonyl)-2-azabicyclo[2.2.1]heptan-3-one and 10 mL of a 70% aqueous solution of ethylamine (by weight). The mixture is heated for 4 hours at 60° C. while stirring. After cooling, the excess triethylamine and water is eliminated under reduced pressure. After drying under reduced pressure, one thus obtains 98% yield of 650 mg of 2R,3S-isopropylidenedioxy-4-R-t-butoxycarbonylamino-1-S-ethylaminocarbonyl cyclopentane, the structure of which is confirmed by the N.M.R. spectrum of the proton, and the rotatory power of which is $[a]^D_{20}=15.0$ (c=1; methanol).

To a solution of 200 mg of 2R,3S-isopropylidenedioxy-4-R-t-butoxycarbonylamino-1-S-ethylaminocarbonyl cyclopentane in 1.6 mL of anhydrous dichloromethane is added 275 ml of trifluoroacetic acid. The mixture is stirred overnight at a temperature of approximately –5° C. The reaction mixture is poured into 4 mL of 2.5N aqueous sodium carbonate. The organic layer is concentrated under reduced pressure at a temperature below 25° C. One thus obtains 125 mg of a product which is dissolved in 0.5 mL tetrahydrofuran. To this solution is added 70 mg of benzoic acid. After cooling the solution obtained to a temperature of approximately 0° C., the crystals obtained are separated by filtration and washed in pentane. One thus obtains 138 mg of 2R,3S-isopropylidenedioxy-4R-amino-1S-ethylaminocarbonyl cyclopentane benzoate.

EXAMPLE 7b

Preparation of 2R,3S-isopropylidenedioxy-4R-amino-1S-ethylaminocarbonylcyclopentane trifluoroacetate In a 25-mL autoclave, equipped with a magnetic stirrer, 1.47 g of 5R-6S-isopropylidenedioxy-2-(t-butoxycarbonyl)-2-azabicyclo[2.2.1]heptan-3-one in a solution in 10 mL of anhydrous toluene is introduced, followed by approximately 0.7 mL of ethylamine. The autoclave is closed and then heated at a temperature between 90° and 100° C. for 21 hours. After cooling, the toluene is evaporated, and the dissolution is carried out with 10 mL of dichloromethane and 10 mL of water. After decanting, the organic phase is washed with 10 mL of water. The combined aqueous layers are washed in 10 mL of dichloromethane. The combined organic phases are washed with 10 mL of a saturated sodium chloride solution and then dried over sodium sulfate. After filtration and concentration to dryness at a reduced pressure, the yield consists of 1.58 g of a product containing 95% 2R,3S-isopropylidene-dioxy-4-R-t-butoxycarbonylamino-1-S-ethylaminocarbonylcyclopentane, whose structure is confirmed by the NMR spectrum, which, determined in dimethyl sulfoxide-d6, shows the following chemical shifts: 0.95 (t, 3H); 1.14 (s, 3H); 1.31 (s, 12H); 1.55 (m, 1H); 2.11 (m, 1H); 2.64 (m, 1H); 3.00 (qi, 2H); 3.77 (m, 1H); 4.23 (m, 1H); 4.54 (m, 1H); 7.07 (d, 1H); 8.12 (t, 1H).

In a 25-mL flask, 1.22 g of 2R,3S-isopropylidenedioxy-4R-t-butoxycarbonylamino-1S-ethylaminocarbonylcyclopentane and 10 mL of dichloromethane are introduced. At a temperature of approximately 25° C., 0.85 g of trifluoroacetic acid is added with stirring. After 6 hours of stirring and concentration to dryness, the yield consists of 1.16 g of 2R,3S-isopropylidenedioxy-4R-amino-1S-ethylaminocarbonylcyclopentane trifluoroacetate, whose structure is confirmed by the NMR spectrum, which, determined in dimethyl sulfoxide-d6, shows the following chemical shifts: 0.79 (t, 3H); 1.03 (s, 3H); 1.19 (s, 3H); 1.42 (m, 1H); 2.05 (m, 1H); 2.52 (m, 1H); 2.89 (qi, 2H); 3.04 (m, 1H); 4.16 (m, 1H).

EXAMPLE 7c

Preparation of 2R,3S-isopropylidenedioxy-4R-amino-1S-ethylaminocarbonyl cyclopentane To a solution of 167 mg of 5R,6S-isopropylidenedioxy-2-(t-butoxycarbonyl)-2-azabicyclo[2.2.1]heptan-3-one in 1 mL of dichloromethane, cooled to 0° C., is added 90 ml of trifluoroacetic acid. The temperature is allowed to rise to 23° C. over 40 minutes, then stirred for 22 hours at this temperature. Another 90 ml of trifluoroacetic acid is added and then stirred for another one hour at a temperature of 23° C. After evaporating under reduced pressure, one obtains 123 mg of 5R,6S-isopropylidenedioxy-2-azabicyclo[2.2.1]heptan-3-one, the purity of which, determined by high-performance liquid chromatography, is approximately 92%, and the structure of which is confirmed by the N.M.R. spectrum of the proton.

A solution of 10 g of 5R,6S-isopropylidenedioxy-2-azabicyclo-[2.2.1]heptan-3-one in 100 mL in a 70% aqueous solution of triethylamine (by weight) is heated to 110° C. for 20 hours under standard pressure. After cooling, the excess triethylamine is eliminated under reduced pressure, then washed with dichloromethane to eliminate the starting product that did not react. The aqueous layer is then concentrated and dried. One thus obtains 10.54 g of 2R,3S-isopropylidenedioxy-4R-amino-1S-ethylaminocarbonyl cyclopentane.

The present invention may be embodied in other specific forms without departing from the spirit or essential attributes thereof.

We claim:

1. A method for the preparation of a compound of formula

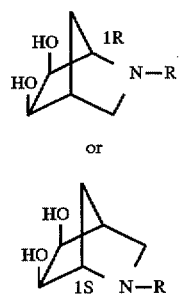

(I)

or

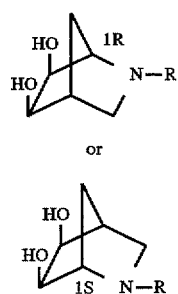

(I')

wherein R represents a hydrogen atom, comprising hydrogenating a compound of formula

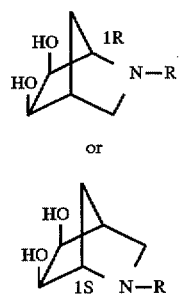

(I)

or

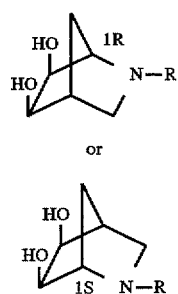

(I')

wherein R represents respectively a group of formula

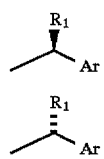

(II)

$$\text{R}_1 \text{—Ar}$$ (II')

wherein $R_1$ represents an alkyl group containing 1–4 carbon atoms and Ar represents a phenyl or α- or β-naphthyl group, optionally substituted by one or more atoms or groups, which may be identical or different, selected from halogen atoms and alkyl groups containing 1–4 carbon atoms, alkoxy groups containing 1 to 4 carbon atoms, or nitro groups, with hydrogen in the presence of a catalyst in an organic solvent selected from aliphatic alcohols containing 1–3 carbon atoms.

2. The method according to claim 1 wherein $R_1$ represents a methyl or ethyl group and Ar represents a phenyl group, optionally substituted by one or more methyl or methoxy groups.

3. The method according to claim 1 wherein $R_1$ represents a methyl group and Ar represents a phenyl group.

4. A method for the preparation of a compound of formula VIII

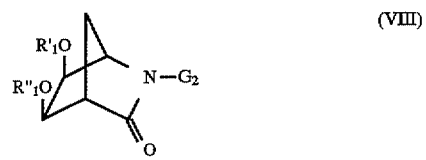

(VIII)

wherein $R'_1$ and $R''_1$, which are identical or different, represent an aliphatic organic acid group containing 2–4 carbon atoms or aromatic acid group, or $R'_1$ and $R''_1$ taken together form a methylene group whose carbon atom is optionally substituted by one or more groups, which may be identical or different, selected from alkyl groups containing 1–4 carbon atoms, which can be taken together with the carbon atom to which the alkyl groups are attached to form an alicyclic group containing 5 or 6 carbon atoms, or phenyl groups, and $G_2$ represents a hydrogen atom or a protecting group of an amino group, comprising:

a) esterifying or acetalating a compound of formula I to protect the hydroxyl moieties thereof:

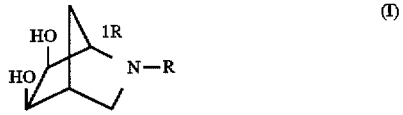

(I)

wherein R represents a hydrogen atom or a group of formula II:

(II)

wherein $R_1$ represents an alkyl group containing 1–4 carbon atoms and Ar represents a phenyl or α- or β-naphthyl group, optionally substituted by one or more atoms or groups, which may be identical or different, selected from halogen atoms and alkyl groups containing 1–4 carbon atoms, alkoxy groups containing 1 to 4 carbon atoms, or nitro groups, with hydrogen in the presence of a catalyst in an organic solvent selected from aliphatic alcohols containing 1–3 carbon atoms, to yield a compound of formula VI

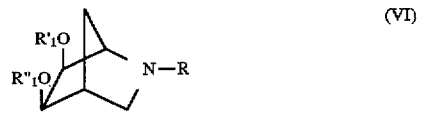

(VI)

wherein R, $R'_1$ and $R''_1$ are defined as above;

b) transforming the compound of formula VI to a compound of formula VII:

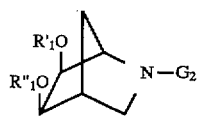

(VII)

wherein R'$_1$ and R"$_1$ are defined as above, and G$_2$ represents a protecting group of the nitrogen atom, by either i) hydrogenating the compound of formula VI, in which R represents a group of formula II and protecting the nitrogen atom with a protecting group, wherein the hydrogenating and protecting are optionally conducted simultaneously, or ii) protecting the nitrogen atom on the compound of formula VI, wherein R represents a hydrogen atom, with a protecting group; and then c) oxidizing the compound of formula VII to the compound of formula VIII.

5. The method according to claim 4, wherein the esterifying or acetalating according to step a) is carried out using an aliphatic acid containing 2–4 carbon atoms or an aldehyde or ketone, optionally in the form of an acetal in the presence of an acid in an inert organic solvent at a temperature between 50° C. and the boiling point of the reaction mixture.

6. The method according to claim 4, wherein the hydrogenating according to step b) is carried out using hydrogen in the presence of a catalyst.

7. The method according to claim 4, wherein when G$_2$ represents a t-butoxycarbonyl group, the hydrogenating and protecting according to step b) are carried out simultaneously using hydrogen in the presence of a catalyst and di-t-butyl dicarbonate in an aliphatic alcohol containing 1–3 carbon atoms at a temperature between 0° C. and 50° C.

8. The method according to claim 4, wherein the oxidizing according to step c) is carried out using RuO$_4$, which is optionally generated in situ in the presence of an oxidant.

9. A method for the preparation of a compound of formula VIII

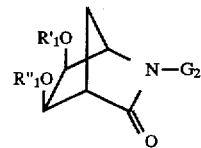

(VIII)

wherein R'$_1$ and R"$_1$, which are identical or different, represent an aliphatic organic acid group containing 2–4 carbon atoms or aromatic acid group, or R'$_1$ and R"$_1$ taken together form a methylene group whose carbon atom is optionally substituted by one or more groups, which may be identical or different, selected from alkyl groups containing 1–4 carbon atoms, which can be taken together with the carbon atom to which the alkyl groups are attached to form an alicyclic group containing 5 or 6 carbon atoms, or phenyl groups, and G$_2$ represents a hydrogen atom or a protecting group of an amino group, comprising oxidizing a compound of formula VI

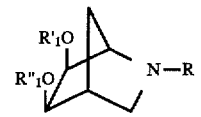

(VI)

wherein R'$_1$ and R"$_1$ are defined above and R represents a hydrogen atom, with RuO$_4$, which is optionally generated in situ in the presence of an oxidant, to obtain a lactam compound, and then protecting the nitrogen of the lactam by reacting the lactam with di-t-butyl dicarbonate in an aliphatic alcohol containing 1–3 carbon atoms at between 0° C. and 50° C.

\* \* \* \* \*